United States Patent
Koertge et al.

(10) Patent No.: US 8,594,773 B2
(45) Date of Patent: Nov. 26, 2013

(54) DENOISING AND ARTIFACT REJECTION FOR CARDIAC SIGNAL IN A SENSIS SYSTEM

(75) Inventors: Detlef W Koertge, Carpentersville, IL (US); Hongxuan Zhang, Palatine, IL (US); Bryon Pelzek, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 552 days.

(21) Appl. No.: 12/891,831

(22) Filed: Sep. 28, 2010

(65) Prior Publication Data

US 2011/0015532 A1    Jan. 20, 2011

Related U.S. Application Data

(63) Continuation-in-part of application No. 11/831,143, filed on Jul. 31, 2007, now abandoned.

(60) Provisional application No. 60/913,905, filed on Apr. 25, 2007.

(51) Int. Cl.
*A61B 5/0428* (2006.01)

(52) U.S. Cl.
USPC .......................................... 600/509; 128/901

(58) Field of Classification Search
USPC ......... 600/508, 509; 702/69, 75, 84; 128/901, 128/902
See application file for complete search history.

(56) References Cited

U.S. PATENT DOCUMENTS

| | | | |
|---|---|---|---|
| 4,751,931 A * | 6/1988 | Briller et al. | 600/513 |
| 5,188,117 A | 2/1993 | Steinhaus et al. | |
| 5,983,162 A | 11/1999 | Huang | |
| 6,405,076 B1 | 6/2002 | Taylor et al. | |
| 6,537,288 B2 | 3/2003 | Vargas et al. | |
| 7,070,566 B2 | 7/2006 | Medero et al. | |
| 7,212,850 B2 | 5/2007 | Prystowsky | |
| 2007/0038382 A1* | 2/2007 | Keenan | 702/19 |
| 2009/0292180 A1* | 11/2009 | Mirow | 600/301 |
| 2011/0257556 A1* | 10/2011 | Guo et al. | 600/544 |

OTHER PUBLICATIONS

Liang et al., "Application of the empirical mode decomposition to the analysis of esophageal manometric data in gastroesophageal reflux disease", Biomedical Engineering, IEEE Transactions Biomedical Engineering, vol. 52, No. 10, Oct. 2005, pp. 1692-1701.

* cited by examiner

Primary Examiner — Kennedy Schaetzle
Assistant Examiner — Erica Lee
(74) Attorney, Agent, or Firm — Peter R. Withstandley

(57) ABSTRACT

A system denoises and rejects artifacts from cardiac signals, by accepting a cardiac signal from a patient, processing the cardiac signal from the patient using a frequency band width controllable choke to separate the cardiac signal into predefined frequencies, filtering each of the predefined frequencies to remove dynamic common noise, joining each of the predefined frequencies into a cardiac signal without the dynamic common noise, and providing feedback control of the filtering of each of the predefined frequencies.

19 Claims, 7 Drawing Sheets

DENOISING AND ARTIFACT REJECTION FOR CARDIAC SIGNAL IN A SENSIS SYSTEM

CROSS-REFERENCE TO RELATED APPLICATIONS

This is a United States Continuation in Part Application of non-provisional application Ser. No. 11/831,143 claiming priority of U.S. provisional patent application Ser. No. 60/913,905 the entirety of which application is incorporated by reference herein.

FIELD OF THE INVENTION

The present invention relates to noise and artifact interference reduction. More specifically, the invention provides a method and apparatus to suppress noise and artifacts encountered during evaluation of cardiac signals for medical patients.

BACKGROUND INFORMATION

Cardiac monitoring equipment can use different approaches and strategies for noise cancellation or reduction and artifact reduction. These conventional approaches include notch filtering for 50/60 Hertz electrical artifacts or low pass filtering for high frequency emission noise. These conventional approaches, however, have several shortcomings that are troublesome for medical personnel performing evaluations.

A first drawback to conventional approaches is that frequency analysis based filtering techniques can not efficiently remove common mode noise and artifact interference that share the same frequency band with cardiac signals (commonly known as overlapping signals).

A second drawback to conventional approaches is that fixed low or high frequency band pass filtering in current demising and artifact rejection methods can not effectively track and cancel dynamic noise and artifacts (especially broad band noise and semi-white noise), such as voltage/current leakage noise generated from use of bovie knife and cardiac ablators.

Another drawback to conventional approaches is that these methods are designed for linear signal processing and analysis that may not effectively reduce the non-linear and non-stationary noise and artifacts for the cardiac signals.

A further drawback to conventional approaches is that denoising methods do not have enough intrinsic data analysis and characterization of the noise and interference in the cardiac signals which greatly limit the application and efficiency of the noise removal and artifact rejection.

There is a need to provide a method and apparatus of denoising signals and performing artifact rejection related to cardiac signals from medical patients, wherein the signals and artifacts removed overlap with the cardiac signals.

There is a further need to provide a method and apparatus that can effectively track and cancel dynamic noise and artifacts such as voltage/current leakage noise generated from use of medical instruments such as bovie knife and cardiac ablators.

There is also a need to provide a method and apparatus that can evaluate and process non-linear and non-stationary noise as well as artifacts for cardiac signals. There is a further need to provide a method and apparatus that provides sufficient intrinsic data analysis and characterization of the noise and interference in the cardiac signals to overcome the conventional method limitations for efficiency of the noise removal and artifact rejection

SUMMARY

It is therefore an objective to provide a method and apparatus of denoising signals and performing artifact rejection related to cardiac signals from medical patients, wherein the signals and artifacts removed overlap with the cardiac signals.

It is also an objective to provide a method and apparatus that can effectively track and cancel dynamic noise and artifacts such as voltage/current leakage noise generated from use of medical instruments such as bovie knife and cardiac ablators.

It is a further objective to provide a method and apparatus that can evaluate and process nonlinear and non-stationary noise as well as artifacts for cardiac signals.

It is a still further objective to provide a method and apparatus that provides sufficient intrinsic data analysis and characterization of the noise and interference in the cardiac signals to overcome the conventional methods limitations for efficiency of the noise removal and artifact rejection.

The objectives achieved as illustrated and described. An embodiment of the invention provides a method for denoising and rejecting artifacts from cardiac signals by accepting a cardiac signal from a patient and separating the cardiac signal into signals in predefined frequency bands. The method includes filtering each of the signals in the predefined frequency bands to remove dynamic noise, joining filtered signals of each of the predefined frequency bands into a cardiac signal without the dynamic noise; and providing a feedback control signal to control the filtering of each of the predefined frequency bands.

The filtering of each of the predefined frequencies to remove dynamic noise is accomplished by identification of interference signals from medical instruments and elimination of noise related to the medical instruments. The method may also be performed such that the dynamic common noise removed is a non-linear signal.

In another embodiment of the invention, the controllable choke separating the signals from the patient is controlled through a computer programmable selection that decreases common mode noise. The filtering of each of the predefined frequencies may be accomplished through empirical mode decomposition processing.

An embodiment of the invention also provides a method for denoising and rejecting artifacts from cardiac signals, comprising the steps of accepting a cardiac signal from a patient, separating the cardiac signal from the patient into predefined frequencies, filtering each of the predefined frequencies to remove dynamic noise, and joining each of the predefined frequencies into a cardiac signal without the dynamic noise. The filtering of each of the predefined frequencies may be accomplished through empirical mode decomposition processing.

In another embodiment, the filtering of each of the predefined frequencies to remove common mode noise is accomplished by identification of interference signals from medical instruments and elimination of noise related to the medical instruments. The dynamic noise removed may be a non-linear signal.

In another embodiment of the invention a program storage device readable by machine, tangibly embodying a program of instructions executable by the machine to perform method steps for denoising and rejecting artifacts from cardiac signals, comprising the steps of accepting a cardiac signal from a patient, separating the cardiac signal from the patient into predefined frequencies; filtering each of the predefined frequencies to remove dynamic noise, joining each of the predefined frequencies into a cardiac signal without the dynamic noise, and providing a feedback control to the filtering of each of the predefined frequencies.

In an embodiment of the invention, the filtering of each of the predefined frequencies is through empirical mode decomposition processing. In another embodiment of the invention, the filtering of each of the predefined frequencies to remove dynamic noise is accomplished by identification of interference signals from medical instruments and elimination of noise related to the medical instruments. Additionally, the dynamic noise removed is a non-linear signal.

In another exemplary embodiment of the invention, a program storage device readable by machine, tangibly embodying a program of instructions executable by the machine to perform method steps for denoising and rejecting artifacts from cardiac signals is presented. The method accomplished comprises accepting a cardiac signal from a patient, separating the cardiac signal from the patient into predefined frequencies, filtering each of the predefined frequencies to remove dynamic common noise, and joining each of the predefined frequencies into a cardiac signal without the dynamic noise. The filtering of each of the predefined frequencies is through empirical mode decomposition processing. The filtering of each of the predefined frequencies to remove dynamic noise is accomplished by identification of interference signals from medical instruments and elimination of noise related to the medical instruments. The dynamic common noise removed is a non-linear signal.

In an additional exemplary embodiment, the controllable choke separating the signals from the patient is controlled through a computer programmable selection that decreases common mode noise.

An embodiment of the present invention also provides an apparatus for denoising signals from a medical patient, comprising a frequency band width controllable choke, the choke configured to accept signals from the medical patient and separate the signal into defined frequencies, at least one filter to accept the defined frequencies produced by the frequency band width controllable choke, and a feedback control connected to the at least one filter. The apparatus may further comprise a software control and calibration arrangement connected to the frequency band width controllable choke, the software control and calibration arrangement configured to control the choke.

DETAILED DESCRIPTION

An embodiment of the invention provides an efficient method 100 and apparatus 200 for cardiac signal denoising and artifact rejection. The embodiment of the invention provides both adaptive programmable hardware based filters 208, 210 and 212 as well as signal decomposition/reconstruction. In the invention, dynamic noise is defined by an amplitude/frequency/energy distributions of noise that is/are changeable. In an embodiment of the present invention, the adaptive multi-frequency band (at least two frequency band filters) and automatic close-loop (feedback) are used to achieve real-time gain adjustment of the multi-frequency band and to obtain the best signal noise ratio. Hence there is an optimization issue for the multi-frequency band control:

$$\Phi(\text{signal}) = f(A_1 + A_2 + \ldots + A_n)$$

$\Phi(\bullet)$ is the function value of the signal noise ratio; $f(\bullet)$ is the function to calculate and summarize the signal; $A_i$ is the gain of the $i^{th}$ frequency band. The filtering strategy can achieve the best the signal quality, if $\Phi(\text{signal})$ can reach the biggest value. Common mode noise is conducted on all lines in the same direction, such as EMI noise and background/environmental noise.

In patient monitoring, high quality signals are the basis for proper diagnosis and correct medical treatment decision. The minute signals from patient, however, are usually in millivolt (mV) or microvolt (uV) range. These very low level signals are easily distorted and affected by noise, such as electrical emission noise (environmental noise), patient movement and respiration (bio-artifacts), etc.

Figure 1:
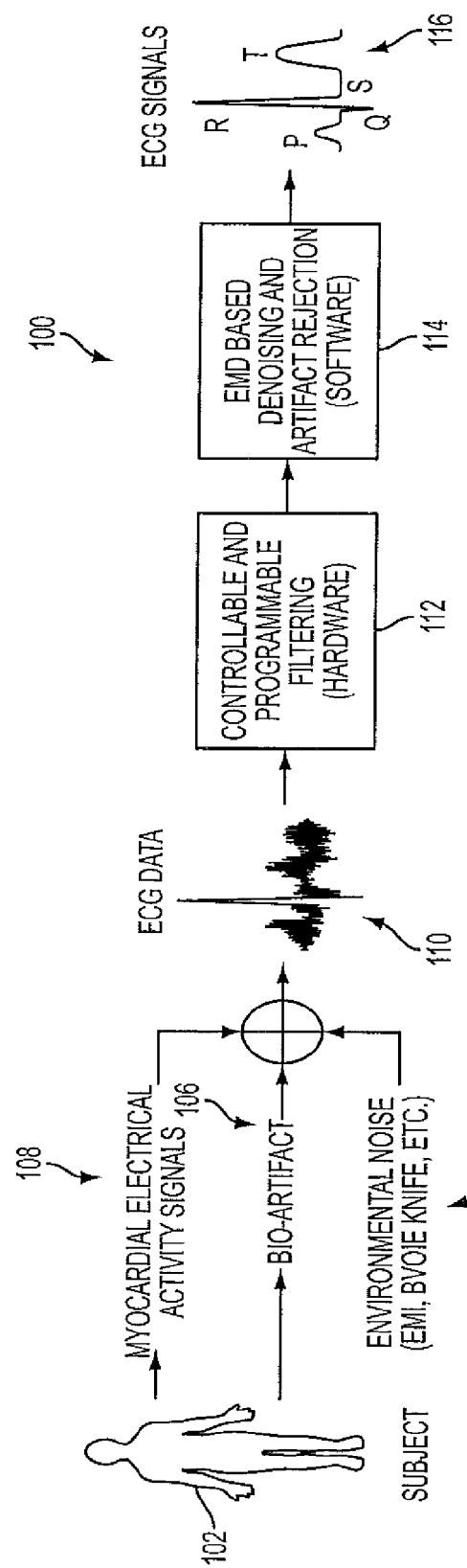
FIG. 1 is a signal denoising/artifact rejection method and system structure, according to invention principles.

This embodiment of the invention provides both a hardware and software combined method 100 for patient signal demising, especially for the cardiac electrophysiological activities (ECG signals). Referring to FIG. 1, an embodiment of the invention is provided for conducting denoising and artifact rejection of cardiac signals from a patient. In FIG. 1, a surface ECG signal is used to describe an example of the denoising strategies, but the method 100 presented may comprise applications in any kind of signals, such as pressure signals, intra-cardiac electrograms, invasive and non-invasive. The processing method 100 takes ECG data 110 from a subject 102 for analysis. The ECG data 110 includes myocardial signals 108, bio artifacts 106 and environmental noise 104. The environmental noise 104 may include signals from equipment, such as surgical equipment or general background electrical interference. The total ECG data 110 is then subjected to controllable/programmable filtering 112. In step 114, an EMD based denoising is then conducted on the ECG data 110. The bio artifacts 106 and the environmental noise 104 are removed from the myocardial signals 108 resulting in clean ECG signals 116 that may be analyzed.

Figure 2:
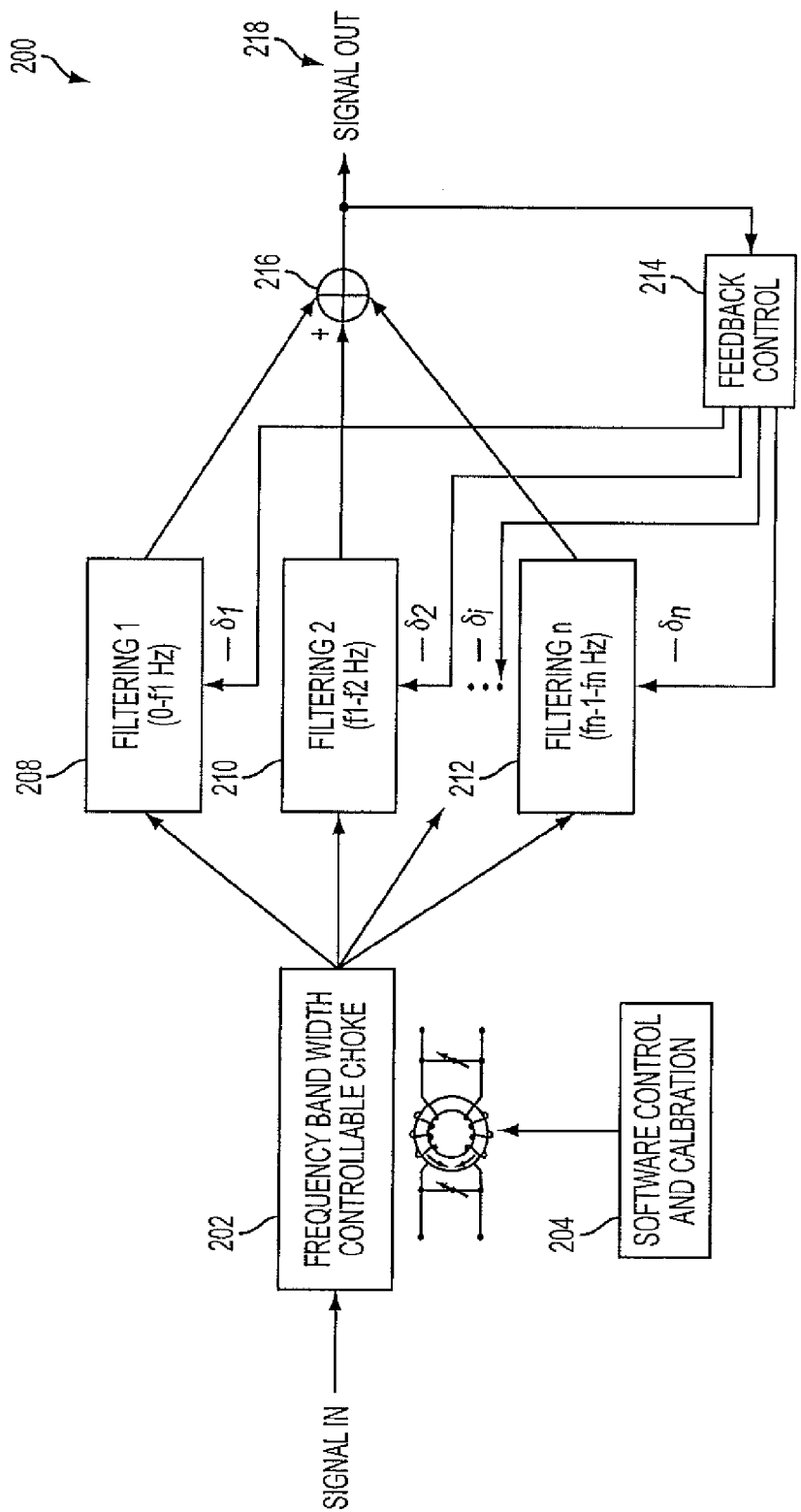
FIG. 2 is a hardware based filtering apparatus for a frequency band width controllable choke for dynamic common noise and adaptive tunable frequency band programmer, according to invention principles.

In an embodiment of the invention, a hardware based denoising and artifact rejection apparatus 200 is provided. The apparatus 200 based embodiment includes a common mode noise controller and adaptive tunable frequency and programmer. The common noise controller apparatus 200 receives input in the form of signals, in the present embodiment cardiac signals, and decreases any noise and artifact effects present during a cardiac operation. Referring to FIG. 2, the apparatus 200 includes a frequency based choke 202 and three filters 208, 210, 212 and a feedback control 214.

During cardiac operations, for example, a bovie knife is used to allow the surgeon to accurately modify tissues present within the patient. The usage of the bovie knife, however, generates dynamic noise (electrical signals) to every data acquisition sensor used for patient monitoring. Concurrently, the use of the bovie knife leads to voltage and current leakages to the patient, both of which may shift both signal and GND of the biomedical instrumentation. To complicate matters, the frequency band width of the leaked noise is dynamic and shifting/changing during the operation. This common mode noise, however, is controlled in an embodiment of the invention by a filtering choke 202 that is efficiently controlled and calibrated by software 204. The frequency band width controllable choke 202 technology used in an embodiment of the invention is connected to a feedback controllable apparatus 214 for automatic and adaptive adjustment of the signal frequency band width.

The hardware based filtering apparatus 200 is constructed from two specific parts. The filtering apparatus 200 has a frequency band width controllable choke 202 for dynamic noise previously described in FIG. 1. The apparatus 200 has an adaptive tunable frequency band programmer and controller 204 that can decrease the effects of the common mode noise in some specific frequency band width.

The adaptive tunable frequency programmer in the filtering and denoising hardware arrangement 200 adaptively control signals as well as noise in different bandwidths. In an embodiment of the invention, the ECG signal from the patient and noise generating devices has a frequency band of 0-200 Hz. The frequency band controller greatly decreases the noise in specific bands, such as 50-60 Hz, without attenuating ECG signals in other frequency bands. Based on the feedback of the signal that is provided, the feedback control arrangement 214 analyzes the signal to noise ratio (SNR) of different frequency bands and adjusts the filtering parameters of noisy band. In the illustrated embodiment, there are three bands that are evaluated. After filtering, the signals are combined 216 to produce a signal out 218. The adaptive tunable frequency denoising system 200 accepts a cardiac signal from a patient and separates the cardiac signal into signals in predefined frequency bands. System 200 filters each of the signals in the predefined frequency bands to remove dynamic noise and joins filtered signals of each of the predefined frequency bands into a cardiac signal without the dynamic noise. System 200 provides a feedback control signal to control the filtering of each of the predefined frequency bands.

System 200 advantageously employs a frequency band width controllable choke for dynamic common noise rejection and adaptive tunable frequency band programmer and controller that to reduce the effects of the color noise in a particular frequency band width. A signal (e.g. patient surface ECG signal, intra-cardiac signals) is input to frequency band width controllable choke 202 used to decompose the input signal into different sub-signals of specific bandwidth. For example, according to signal characteristics, the input signal (ECG) may be divided into 5 band widths, 0-5 Hz, 5-25 Hz, 25-50 Hz, 50-75 Hz, 75 Hz-200 Hz, (beyond 200 Hz, the ECG signal may be ignored in one embodiment). With the sub-signals in different band width, different filters (filter 1 to n; 208, 210-212) are applied to eliminate the noise, such as 50/60 power line floating noise, respiration noise, patient movement induced noise. According to the environment and situation in a hospital, filters 208, 210-212 of different frequency band width may be manually or automatically adjusted, tuned and controlled adaptively in response to signal to noise ratio and user requirements. For example, in band 0-5 Hz, if the respiration noise or patient movement noise is high, a user or program reduces the magnitude of the filter, e.g. 0-0.5 Hz or 0-2 Hz, to more effectively remove this noise. Although; the signal in the band width may also be reduced, the signal to noise ratio in a particular frequency band is substantially and efficiently improved. Sub-signal components filtered via different frequency band filters, are combined and reconstructed via adder 216. If signal to noise ratio of an input signal is 3:1, in response separating the cardiac signal into signals in predefined frequency bands, filtering each of the signals in the predefined frequency bands to remove dynamic noise and joining filtered signals of each of the predefined frequency bands into a cardiac signal (signal decomposition, frequency band filtering, signal reconstruction), signal to noise ratio of the output signal is 6:1 to 10:1, which improves signal diagnosis accuracy and quality. The tunable techniques used in the exemplary embodiment presented are implemented by the hardware as a closed loop for automatic feedback control. Concurrently the filtering parameter and feedback weight $\delta_i$ are programmed and controlled from the firmware on board or software in the PC (application software).

By adjusting the signal and noise level of different frequency bands, the SNR of the output signal 218 is greatly enhanced compared to non-filtered signals 206. The high quality output signal is achieved by sacrificing the signal in the noisy frequency band. The frequency band of the filters, $\Delta f_i$, in the exemplary embodiment can be tuned and adjusted according to the signal type and application.

The adaptive tunable frequency band programmer based demising strategy is very useful for removing common mode noise in the specific frequency band, such as the ablator noise (450-500 KHz) and power electrical interference (50-60 Hz). Comparing the results of the invention to notch filtering techniques, the adaptive tunable frequency band filtering is more flexible and stability of the filtering is high.

Figure 3:
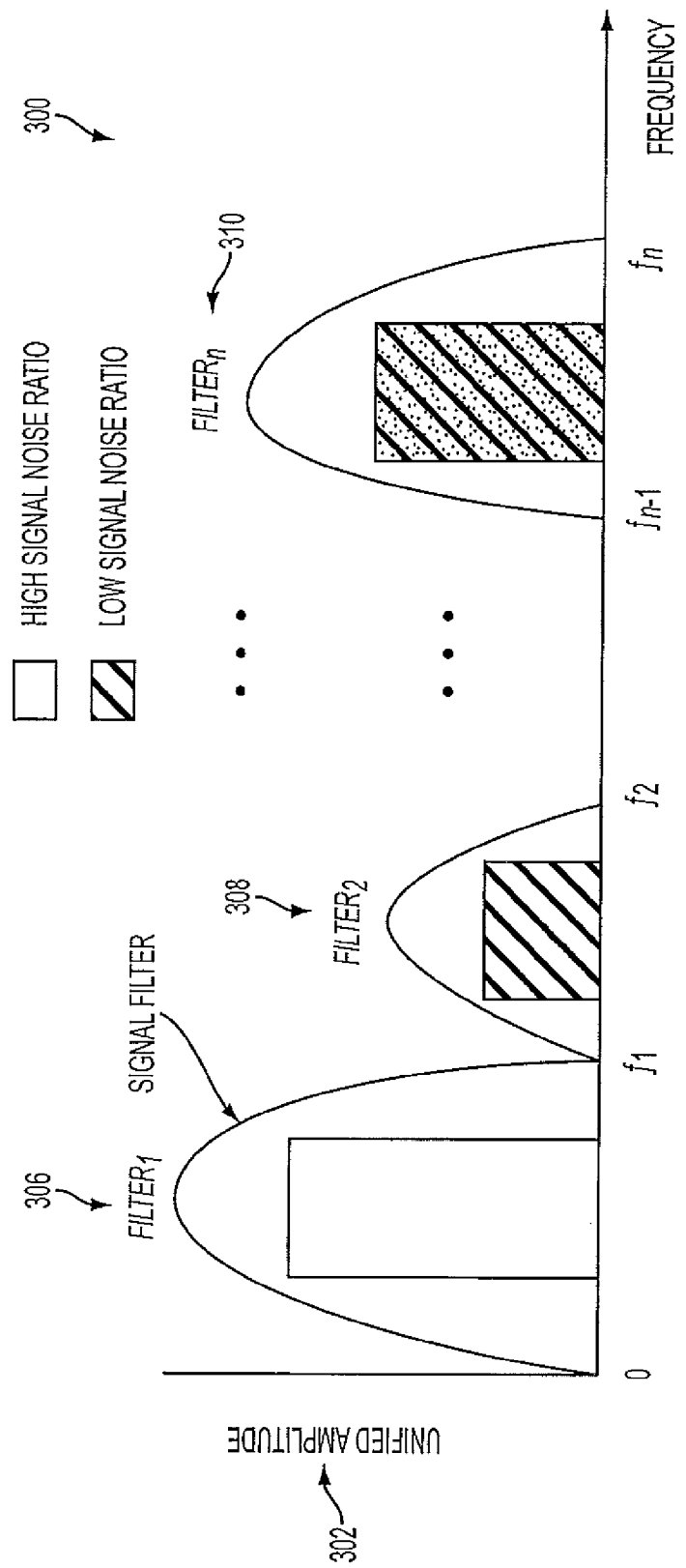
FIG. 3 is a frequency band controlling method for adaptive tunable frequency band programmer, according to invention principles.

Referring to FIG. 3, a graph 300 of unified amplitude 302 verses frequency 304 of signals for an individual is presented. The frequency band controlling strategies of the adaptive tunable frequency band programmer is illustrated. As provided in FIG. 3, the common mode noise is mainly focusing in the frequency band $f_1$-$f_2$ and hence the adaptive feedback controller adjusts the parameter of Filter 2 308 to decrease the noise and artifact effect. By feedback tuning, the output signal quality and SNR are greatly enhanced. As provided with Filter 1 306, a high signal to noise ratio is presented, therefore no adjustments are made for these frequencies. For Filter 3 310, a medium signal to noise ratio is present, therefore no feedback controller adjustment is performed.

FIG. 3 illustrates frequency band control of adaptive tunable frequency band programmer system 200 (FIG. 2). The example in FIG. 3 indicates the color noise is mainly present in the frequency band $f_1$ $f_2$ and hence the adaptive feedback controller adjusts the parameter of Filter 2 to decrease the noise and artifact effect. By feedback tuning, the output signal quality and signal to noise ratio are enhanced. FIG. 3 shows tuning and adjustment for filters 208, 210-212 of different frequency band width (FIG. 2). The signal frequency band width can divided into n sub-frequency bands which are correspond to n sub-signal components. For example filter r1 controls the signal and noise in frequency band width: 0-$f_1$. Usually by controlling the filter (transform function) amplitude and frequency response, a user can eliminate unwanted noise. For instance, setting amplitude threshold to 0 for 0-0.1 Hz in filter r1 removes the DC noise and normal signal shift noise. Filter r2 has a lower frequency magnitude since system 200 or a user determines that noise in this frequency band $f_1$-$f_2$ is excessive and signal to noise ratio in this frequency band is lower, which means filter r2 may need high suppression of signal and noise. Both signal and noise may be reduced by reducing the magnitude of a filter r2 transform function and this may attenuate the signal in this sub-frequency band but result in obtaining an improved signal to noise ratio over the whole signal band width. In the real time world, noise is usually a colorful noise which is typically in a specific band and system 200 improves signal quality at the expense of only a small attenuation in the signal. System 200 also provides a software (signal processing algorithm) based signal filtering method. The signal processing algorithm in the exemplary embodiment of the present invention is an empirical mode function decomposition and reconstruction. Empirical Mode Decomposition (EMD) is a signal processing method for analyzing nonlinear and non-stationary time series. (For example, bovie knife and patient movements always generate non stationary noise and artifacts).

The method of the exemplary embodiment utilizes an EMD algorithm to obtain the decomposed signal components, which may come from the cardiac signals, bio-artifacts, environmental noise, etc. By analyzing the EMD components and sub-signals, the noise based components can be removed prior to EMD signal reconstruction. Hence, the signal to noise ratio of the reconstructed cardiac signal is greatly improved.

Figure 5:
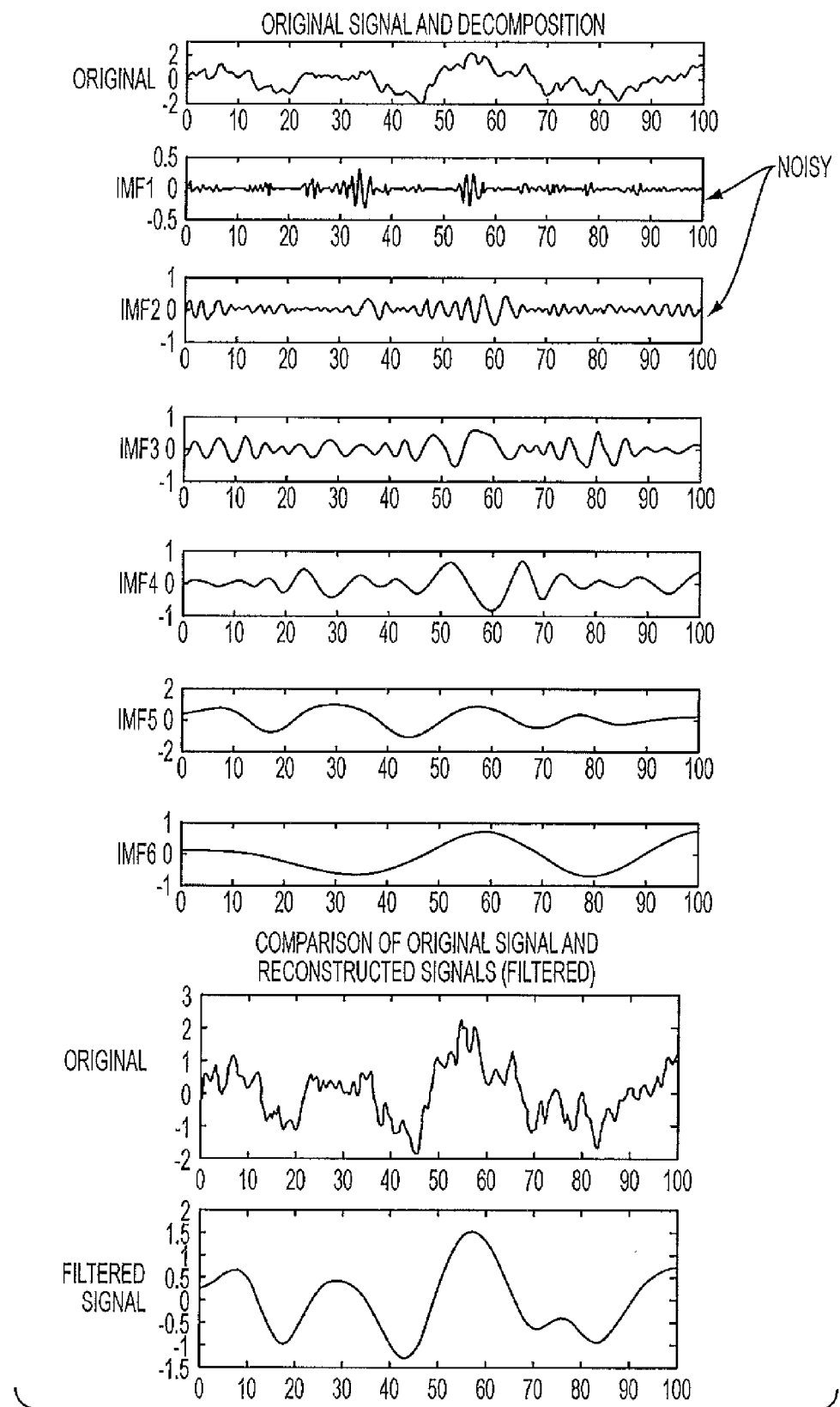
FIG. 5 is a EMD based signal decomposition and reconstruction of the algorithm of FIG. 4, according to invention principles.

FIG. 5 illustrates an example of the EMD algorithm based signal decomposition and reconstruction. The EMD based signal denoising and artifact rejection are not based on frequency or time analysis, but intrinsic signal oscillators and generators. Although described as providing an EMD algorithm based signal decomposition; other algorithms may be used, including, but not limited to independent component analysis (ICA), primary component analysis (PCA), etc. These exemplary types of signal processing algorithms and theories may be also be used for noise removal.

A first step of data analysis is visual examination of the data. From this examination, different scales are identified by a time lapse between the successive alternations of local maxima and minima; and by time lapse between the successive zero crossings.

The interlaced local extrema and zero crossings produce a complicated data output with one undulation superimposed on another, and they, in turn, are riding on other undulations. Each of these undulations defines a characteristic scale of the data. The exemplary embodiment of the invention adopts a time lapse between successive extrema as the definition of the time scale for the intrinsic oscillatory mode. This is accomplished as it gives a fine resolution of the oscillatory modes and also can be applied to data with a non-zero mean, either all positive or all negative values, without zero crossings. The decomposition procedure is adaptive, data-driven, therefore, highly efficient. A systematic method to extract the intrinsic mode functions (IMFs) or component, designated as the sifting process, is presented to accomplish noise and artifact reduction.

EMD methods according to an embodiment of the invention provide strategies to automatically identify the relevant IMFs that contribute to the slow-varying trend in the data. These methods greatly decrease the time consuming of the signal analysis and enhance EMD method application efficiency, especially in the cardiac signal denoising and artifact rejection. Additionally, signal pre-processing, such as filtering, of the decomposed signal components before the reconstruction may be needed and helpful for better SNR and signal quality.

Figure 4:
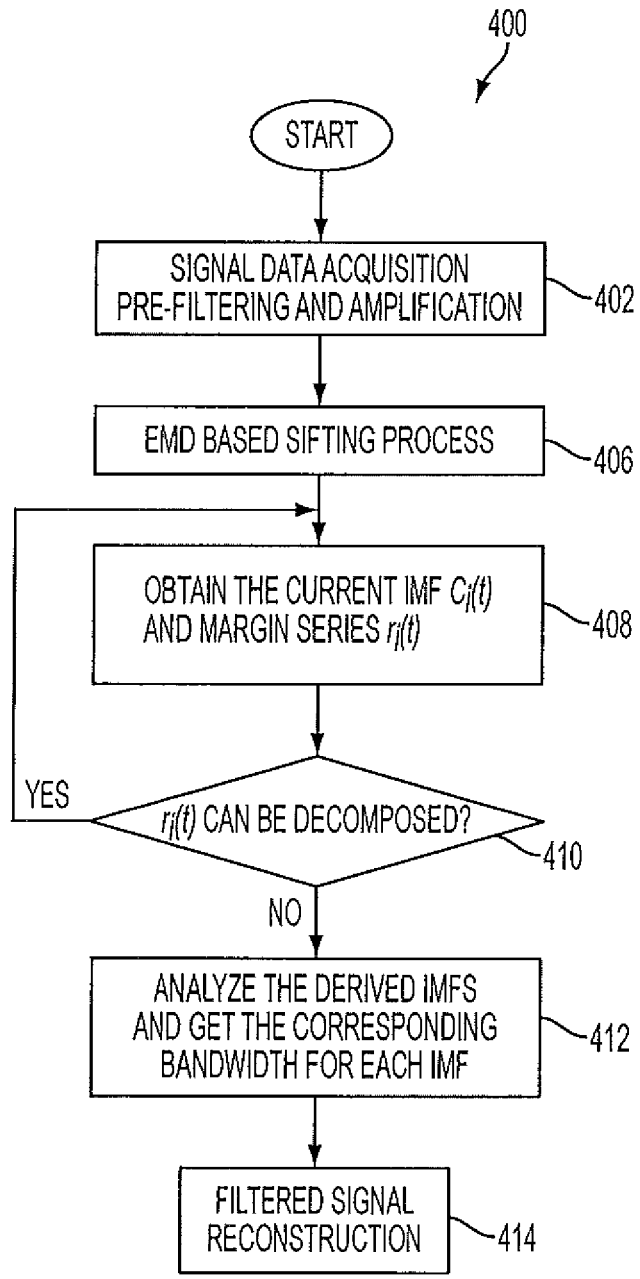
FIG. 4 is a EMD algorithm based signal decomposition and reconstruction, according to invention principles.

Referring to FIG. 4, the procedure 400 of EMD decomposition is provided, according to an embodiment of the invention, that specifies if the number of maxima or minima of data series X(t) is larger than the number of up-zero (or down-zero) crossing points by two, then the series needs to be forced to be stationary. The detailed procedures are as follows:

The method is started 402 from acquiring signal data from a patient 102. Then a EMD based sifting process is accomplished 406. The sifting process is accomplished by obtaining a current IMF 408 (noise components) of the signal. To achieve this, the current IMF noise components, the data must be evaluated such that:

(i) Pick out all of the maxima of the series X(t) and calculate the upper envelop with cubic spline function.
(ii) Pick out all of the minima of the series X(t) and calculate the lower envelop with cubic spline function.

Next, in the non-limiting exemplary embodiment of the invention, the mean envelop $m_1(t)$ of the series X(t) is the mean value of the upper and lower envelops. A new series $h_1$ with low frequency removed is calculated by subtracting the mean envelop from the series X(t):

$$X(t)-m_1(t)=h_1(t)$$

In the exemplary embodiment, $h_1$ is a non-stationary series, so the above procedure must be repeated k times until the mean envelop is approximate to zero, so the first IMF component $C_1(t)$ is obtained:

$$h_{k-1}(t)-m_{1k}(t)=h_{1k}(t)$$

$$C_1(t)=h_{1k}(t)$$

The first IMF component represents the highest frequency component of the original series. The second IMF component $C_2(t)$ is obtained from $r_1(t)$ which is calculated by subtracting the first IMF component from series X(t). Such procedure is repeated until the last margin series $r_n(t)$ cannot be decomposed further 410, here $r_n(t)$ represents the mean value or trend of the original series.

$$r_1(t)-C_2(t)=r_2(t), \ldots, r_n(t)-C_n(t)=r_n(t)$$

Finally, the original series is presented by a stun of the IMF components and a mean value or trend, as provided in step 412:

$$X(t) = \sum_{j=1}^{n} C_j(t) + r_n(t)$$

Since every IMF component (IMFi) is a series with a definite characteristic scale, the sifting procedure actually decomposes the original series to a superimposition of waves with various scales. Every IMF component can be either linear or nonlinear. Lastly, the filtered signal is reconstructed 414.

The embodiment of the invention provides a method and apparatus that allows for superior patient protection by decreasing power leakage and electromagnetic interference that patients are subjected to.

The embodiment of the current invention provides several advantages over conventional techniques, including providing a controllable choke 202 based common noise rejection to reduce dynamic EMI noise.

The embodiment of the invention also provides an adaptive filtering technique that allows the user to enter a frequency band for analysis to decrease color noise from the signal of interest. Furthermore, the embodiment of the present invention provides a cardiac electrophysiological activity extraction via intrinsic signal (resources) decomposition and reconstruction, described as Empirical Mode Decomposition (EMD) processing, to cancel the bio-artifacts and noise.

Figure 6:
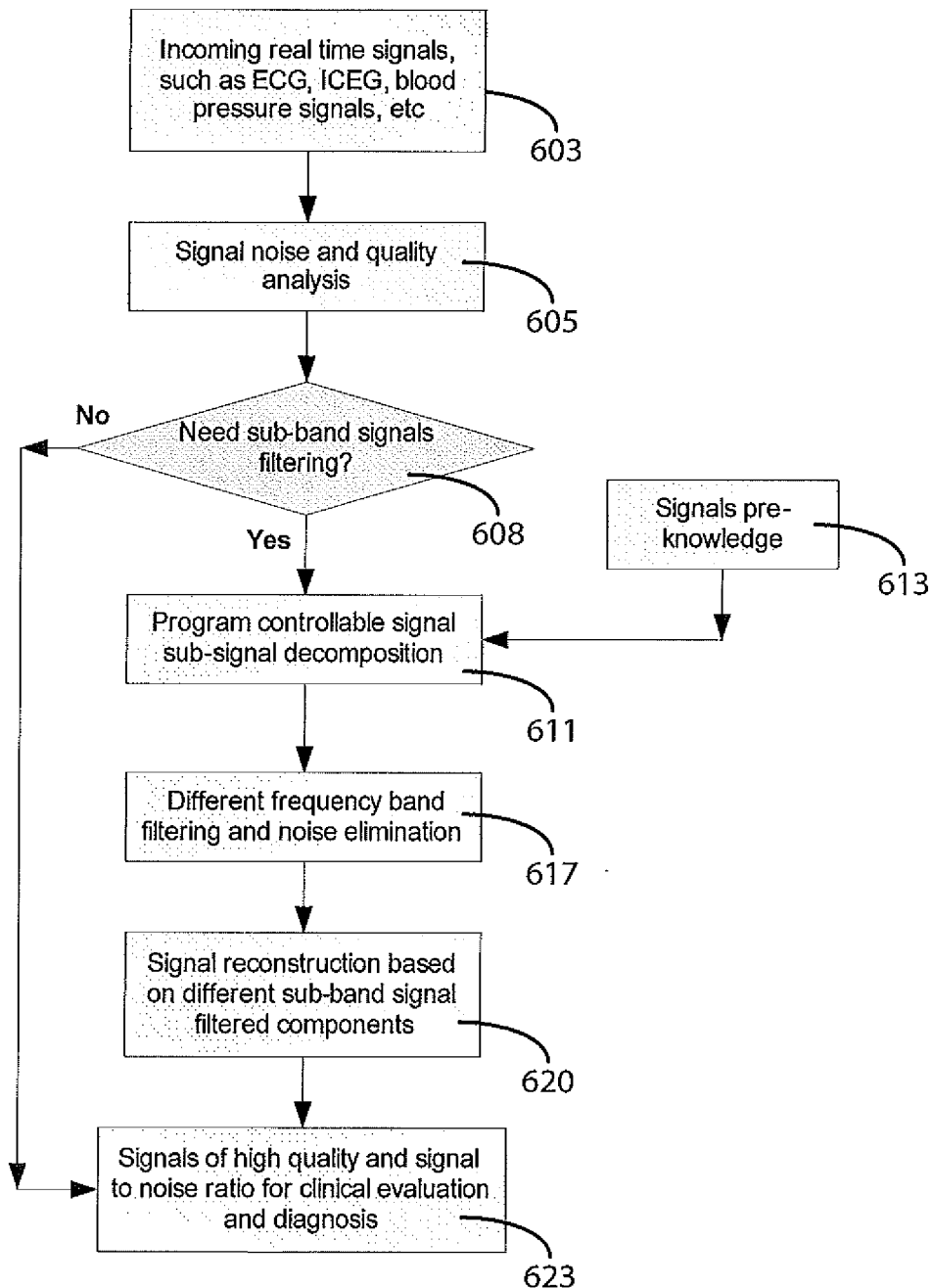
FIG. 6 is a flowchart of a process of multi-frequency band based signal filtering, according to invention principles.

FIG. 6 shows a flowchart of a process for multi-frequency band based signal filtering and demising employed by system 200 (FIG. 2). An input signal acquired in step 603 is analyzed in step 605 to determine signal quality (signal to noise ratio) and to determine if the signal needs sub-band filtering this may be performed by the system or by or user adjustment. If it is determined in step 608 that the signal is of sufficient quality, the process provides the signal for clinical evaluation in step 623 and the process terminates. Otherwise the signal is decomposed in to predetermined sub-bands in step 611 in response to predetermined signal characteristic information acquired in step 613. Signal decomposition into different bands is performed to analyze the signal characteristics and decompose the signal into different frequency bands based on signal and noise band width. This step is performed in response to predetermined information identifying characteristics of known signal types (such as ECG, ICEG, Hemodynamic blood pressure, SPO2, respiration signals, for example) and associated predetermined filter function data. System 200 filters and reduces noises in the different sub-bands in step 617. Sub-frequency band based filtering and each filter band magnitude and frequency response may be tuned, adjusted and controlled automatically or manually by a user. The adder unit is used to join and reconstruct the digital sub-band signals in step 620 to provide the combined signal for output in step 623 having increased signal to noise ratio.

Figure 7:
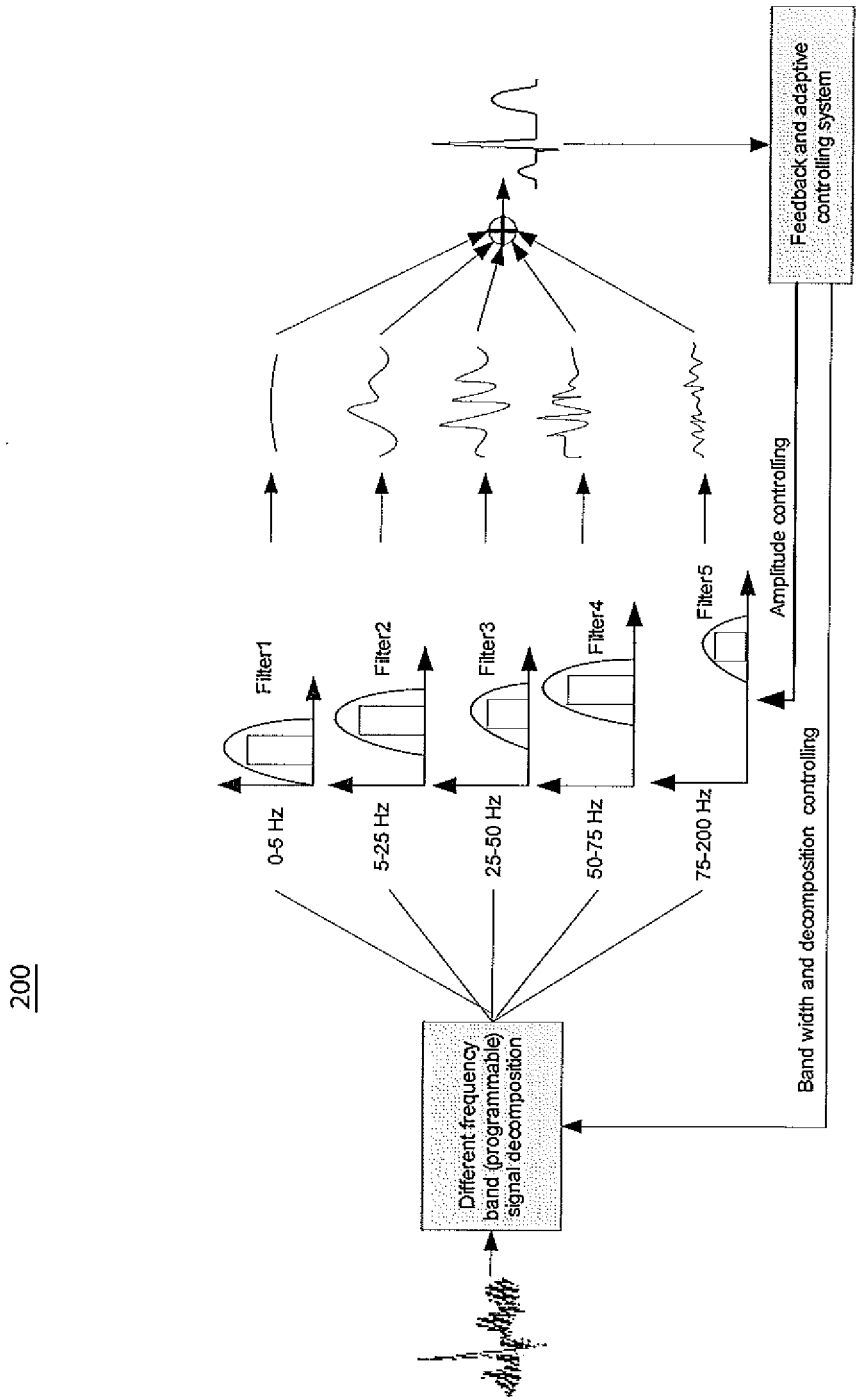
FIG. 7 shows an example of multi-band filtering based signal denoising, according to invention principles.

FIG. 7 shows an example of multi-band filtering based signal denoising employed using system 200 (FIG. 2) to improve signal to noise ratio. A noisy ECG input signal (SNR 3:1) is processed by system 200 to provide a high SNR ECG output signal (SNR10:1). System 200 detects the input signal is noisy and needs to be filtered. The band width control and decomposition unit divides the signal into 5 sub-signal components having 5 corresponding band widths, 0-5 Hz, 5-25 Hz, 25-50 Hz, 50-75 Hz, 75 Hz-200 Hz, respectively. The sub-signal components are filtered in each sub-frequency-band in response to system 200 adaptive control. For example, the DC and signal baseline shift is eliminated in filter band 1. The color noise (bio-noise, such as patient movement) is eliminated in filter band 3. The Semi-white noise and other high frequency noise are removed in filter band 5. The normalized filter amplitude is tuned and adjusted to 0.8, 1, 0.75, 1, and 0.45 for filter 1 to filter 5 in response to signal quality analysis and by using feedback control. The filter amplitude coefficient (for noise suppression and removal) is adaptively tuned and controlled by system 200 or by a user in response to signal quality. For example, if shifting baseline noise is higher during a clinical procedure, the amplitude coefficient of filter 1 is tuned to 0.60-0.75, which reduces noise. There are many methods for signal noise ratio calculation, here signal to noise ratio equals ratio of peak to peak value of a whole ECG signal versus peak to peak value of noise. In ECG signal filtering, the signal peak to peak value is around the QRS complex and noise peak to peak is derived at rest time, such as 100 ms second after a T wave in the ECG cycle.)

Different band widths are employed to control the sub-signal components and reduce signal noise rather than filtering the whole signal with a low pass, high pass or band pass filter, for example. The sub-band component signal filtering is a non-uniform band controlled nonlinear filtering. Following filtering, the sub-component signals are reconstructed into an output signal with improved quality. The system can be implemented in software or hardware or a combination of both. Also the calculation and filtering methods can be used in ICD (implantable cardiac devices) for low complexity and load calculation and signal evaluation.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method for denoising and rejecting artifacts from cardiac signals, comprising:
    accepting a cardiac signal from a patient;
    separating the cardiac signal into signals in predefined frequency bands in the time domain using a frequency band width controllable choke;
    filtering each of the signals in the predefined frequency bands to remove dynamic noise;
    joining filtered signals of each of the predefined frequency bands into a cardiac signal without the dynamic noise; and
    providing a feedback control signal to control the filtering of each of the predefined frequency bands.

2. The method according to claim 1, wherein the filtering of each of the predefined frequency bands to remove dynamic noise is accomplished by identification of interference signals from medical instruments and elimination of noise related to the medical instruments.

3. The method according to claim 1, wherein the dynamic noise removed is a non-linear signal.

4. The method according to claim 1, wherein the signals from the patient are controlled through a computer programmable selection that decreases common mode noise.

5. The method according to claim 1, wherein the filtering of each of the predefined frequencies is through empirical mode decomposition processing.

6. A method for denoising and rejecting artifacts from cardiac signals, comprising:
    accepting a cardiac signal from a patient;
    separating the cardiac signal from the patient into signals in predefined frequency bands in the time domain using a frequency band width controllable choke;
    filtering each of the signals in the predefined frequency bands to remove dynamic noise; and
    joining filtered signals of each of the predefined frequency bands into a cardiac signal without the dynamic noise.

7. The method according to claim 6, wherein the filtering of each of the predefined frequencies is through empirical mode decomposition processing.

8. The method according to claim 6, wherein the filtering of each of the predefined frequency bands to remove dynamic noise is accomplished by identification of interference signals from medical instruments and elimination of noise related to the medical instruments.

9. The method according to claim 6, wherein the dynamic noise removed is a non-linear signal.

10. A program storage device readable by machine, tangibly embodying a program of instructions executable by the machine to perform method steps for denoising and rejecting artifacts from cardiac signals, comprising:
    accepting a cardiac signal from a patient;
    separating the cardiac signal from the patient into signals in predefined frequency bands in the time domain using a frequency band width controllable choke;
    filtering each of the signals in the predefined frequency bands to remove dynamic noise;

joining filtered signals of each of the predefined frequency bands into a cardiac signal without the dynamic noise; and providing a feedback control signal to control the filtering of each of the predefined frequency bands.

11. The device according to claim 10, wherein the filtering of each of the predefined frequencies is through empirical mode decomposition processing.

12. The device according to claim 10, wherein the filtering of each of the predefined frequency bands to remove dynamic noise is accomplished by identification of interference signals from medical instruments and elimination of noise related to the medical instruments.

13. The device according to claim 10, wherein the dynamic noise removed is a non-linear signal.

14. A program storage device readable by machine, tangibly embodying a program of instructions executable by the machine to perform method steps for denoising and rejecting artifacts from cardiac signals, comprising:

accepting a cardiac signal from a patient;

separating the cardiac signal from the patient into signals in predefined frequency bands in the time domain using a frequency band width controllable choke;

filtering each of the signals in the predefined frequency bands to remove dynamic noise; and joining filtered signals of each of the predefined frequency bands into a cardiac signal without the dynamic noise.

15. The method according to claim 14, wherein the filtering of each of the predefined frequencies is through empirical mode decomposition processing.

16. The method according to claim 15, wherein the filtering of each of the predefined frequency bands to remove dynamic noise is accomplished by identification of interference signals from medical instruments and elimination of noise related to the medical instruments.

17. The method according to claim 15, wherein the dynamic noise removed is a non-linear signal.

18. The method according to claim 15, including in the time domain filtering the predefined frequencies produced by the frequency band width controllable choke; and using a feedback control for the filtering of the predefined frequencies.

19. The method according to claim 18, including controlling the frequency band width of the controllable choke.

* * * * *